United States Patent [19]

Engelhardt

[11] Patent Number: 4,947,502
[45] Date of Patent: Aug. 14, 1990

[54] METHOD OF MAKING A DYNAMIC TENSION BONE SCREW

[75] Inventor: John A. Engelhardt, Warsaw, Ind.

[73] Assignee: Boehringer Mannheim Corporation, Indianapolis, Ind.

[21] Appl. No.: 495,352

[22] Filed: Mar. 16, 1990

Related U.S. Application Data

[62] Division of Ser. No. 255,154, Oct. 7, 1988.

[51] Int. Cl.$^5$ ............................................. B23G 9/00
[52] U.S. Cl. .................................. 10/10 R; 10/27 FS; 411/392
[58] Field of Search ............ 10/2, 10 R, 27 R, 27 FS, 10/27 PH; 128/92 YE, 92 YF, 92 YV, 92 ZW, 92 ZZ; 606/65, 66, 70, 105; 411/392, 395, 16, 17

[56] References Cited

U.S. PATENT DOCUMENTS

| | | | |
|---|---|---|---|
| D. 283,591 | 4/1986 | Swanstrom | D8/387 |
| 718,546 | 1/1903 | Tomlinson | 10/27 FS |
| 972,787 | 10/1910 | Huyck | 403/247 |
| 1,204,254 | 11/1916 | Dodds | 411/392 |
| 1,462,925 | 7/1923 | Wilburger | 411/16 X |
| 2,035,497 | 3/1936 | Morse | 411/544 |
| 2,037,156 | 4/1936 | Taplin | 267/264 |
| 2,563,976 | 8/1951 | Torosian | 411/544 |
| 2,856,617 | 10/1958 | Widmann | 10/10 R |
| 2,985,168 | 5/1961 | Jonas et al. | 128/83 |
| 3,051,169 | 8/1962 | Grath | 128/92 R |
| 3,053,555 | 9/1962 | Lahti | D8/387 |
| 3,076,453 | 2/1963 | Tronzo | 128/92 YK |
| 3,373,647 | 3/1968 | Sherock | 411/16 |
| 3,435,526 | 4/1969 | Brancato | 433/174 |
| 3,554,193 | 1/1971 | Konstantinou | 128/92 R |
| 4,227,518 | 10/1980 | Aginsky | 128/92 R |
| 4,537,185 | 8/1985 | Stednitz | 128/92 R |
| 4,589,179 | 5/1986 | Hulting, Jr. | 128/83 |
| 4,621,629 | 11/1986 | Koeneman | 128/92 YE |
| 4,711,232 | 12/1987 | Fischer et al. | 128/92 R |

FOREIGN PATENT DOCUMENTS

| | | | |
|---|---|---|---|
| 674315 | 4/1939 | Fed. Rep. of Germany | 411/392 |
| 2808969 | 9/1979 | Fed. Rep. of Germany | 128/84 C |
| 560269 | 9/1957 | France | 128/92 YF |
| 0652940 | 3/1979 | U.S.S.R. | 128/92 YF |
| 0923533 | 5/1982 | U.S.S.R. | 128/92 YE |
| 1061807 | 12/1983 | U.S.S.R. | 128/92 YF |
| 1022013 | 3/1966 | United Kingdom | 411/16 |

Primary Examiner—E. Michael Combs
Attorney, Agent, or Firm—Perman & Green

[57] ABSTRACT

A dynamic bone fixation screw for rejoining fracture fragments of a bone to their approximate original mutual dispostion. It includes a threaded distal end member for threaded engagment with one of the bone fragments and a head member at a proximal end for engagement with another of the bone fragments. A spring member integral with and extending between the distal end member and the head member enables a predetermined torque to be initially imparted to the bone. When stress relaxation in the bone occurs, the spring member relaxes accordingly while continuing to draw the bone fragments together. The bone screw is fabricated in a unique manner.

2 Claims, 2 Drawing Sheets

FIG. 1.
PRIOR ART
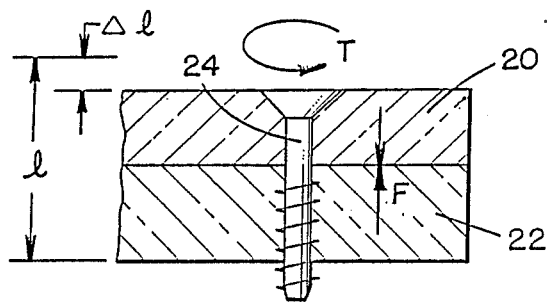
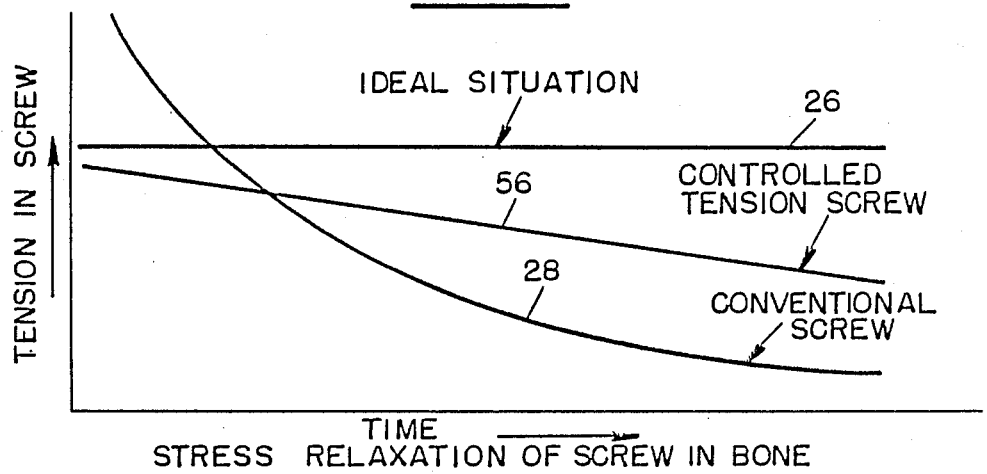
FIG. 2.
FIG. 3.
FIG. 4.
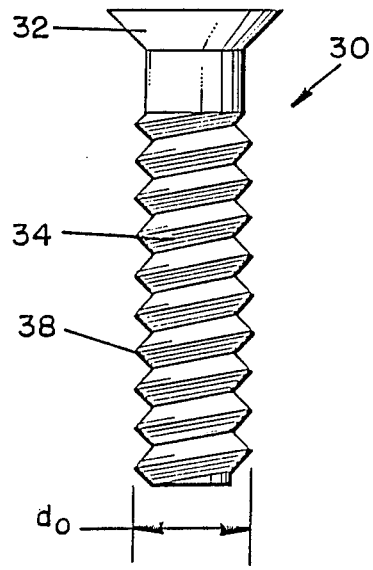
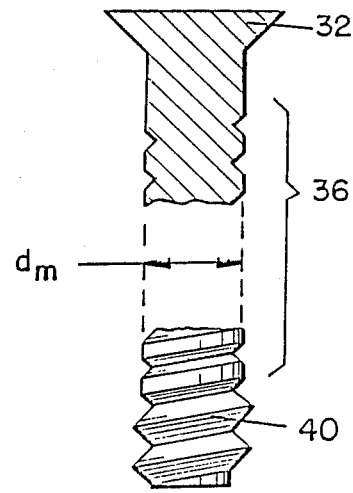

METHOD OF MAKING A DYNAMIC TENSION BONE SCREW

This is a divisional of copending application Ser. No. 07/255,154 filed on 10/7/88.

BACKGROUND OF THE INVENTION

1. Field of the Invention

The present invention relates generally to bone fixation screws and, more particularly, to a bone fixation screw of a dynamic construction and its unique method of fabrication which enables it to relax as the bone relaxes while continuing to draw the bone fragments together.

2. Description of the Prior Art

Upon fracture of a bone, the body's response is to stabilize and heal the fragments in a functional orientation. When a fragment or fragments are displaced in a non-functional or non-anatomical orientation, non-union or malunion can occur. In this instance, open reduction of the fracture may be necessary.

In open reduction, a surgical opening is made, the fracture fragments are realigned, and plates and screws, wire, or other hardware are added to secure the fracture fragments to the bones from whence they came. When a screw is used, whether to secure two fragments together or to secure a plate to the bone, and the screw is tightened, initially, tension in the screw is very high, and holds the fragments together. However, bone is a viscoelastic material and undergoes a phenomenon known as stress relaxation immediately after torque has been applied to the screw. The stress relaxation response is quite pronounced and causes immediate and rapid reduction in the screw tension and, hence, the force holding the fragments together. Furthermore, after a conventional screw is tightened, and the fragment is laterally displaced, as by bending, the rigidity of the screw causes the surrounding bone to fail since the bone is of lower strength and stiffness than the screw. This can lead to failure of fixation and eventual non-union or malunion. Typical constructions of known orthopedic fasteners are disclosed in U.S. Pat. No. 4,537,185 to Stednitz, No. 4,711,232 to Fisher et al, No. 4,227,518 to Aginsky, No. 3,554,193 to Constantinou, and No. 3,051,169 to Grath. In each of these instances, a standard rigid screw is employed which is certain to become loosened relatively rapidly due to the stress relaxation phenomenon previously mentioned.

Another prior art construction of interest in this regard is disclosed in U.S. Pat. No. 2,985,168 to Jonas et al which discloses a bone aligning or splint device which is used to assist in bringing the ends of a pair of fractured fragments of a long bone into alignment and to retain that alignment until the fracture has completely mended. The splint device includes an outer sleeve member received in the intramedullary canal of a first bone fragment with a pin slidably mounted in the sleeve member and a spring above the pin urging it outwardly of the sleeve member. The pin is held in its retracted position until the bone fragments are aligned, then is released under the bias of the spring for reception in the intramedullary canal of the second bone fragment When the splint is in its fully expanded position within the bone fragments, the fragments are in substantial alignment to enable mending to occur. While the Jonas et al splint is satisfactory for its intended purpose of aligning, and maintaining alignment of the bone fragments, it is not intended to, nor does it, actually hold the fragments together.

SUMMARY OF THE INVENTION

It was with knowledge of the mentioned shortcomings of conventional constructions that the present invention has been devised with the result that viscoelastic loosening of bone screws which has heretofore been a persistent problem is now drastically reduced. The invention disclosed is a dynamic bone fixation screw for rejoining fracture fragments of a bone to their approximate original mutual dispositions. The bone screw of the invention is said to be "dynamic" because it is designed to have a stiffness similar to that of the bone it is intended to repair and the force it imparts to the bone fragments changes in accordance with the stress relaxation of the bone. It includes a threaded distal end member for threaded engagement with one of the bone fragments and a head member at a proximal end for engagement with another of the bone fragments. A spring member integral with and extending between the distal end member and the head member enables a predetermined torque to be initially imparted to the bone. As previously noted, when stress relaxation in the bone occurs, the spring member relaxes accordingly while continuing to draw the bone fragments together.

In greater detail, the bone screw of the invention comprises a cancellous or cortical type screw on which a middle segment is of a smaller diameter than the major diameter of the screw thread. Thereupon, the screw is drilled from its head end, or member, through the region of reduced diameter such that the diameter of the bore exceeds that of the root diameter of the threads. This operation perforates the surface of the screw in a spiral fashion along the thread root and thereby results in the formation of a tension spring intermediate the head member and a distal threaded end member. Thereupon, the modified screw is driven into and through a preformed bore in each of the bone fragments to be joined. When the head member abuts an outermost bone fragment, the continued application of torque to the screw draws the distal member away from the head member and stretches the central spring portion. This produces a compressive force between the fragments, drawing them together. The magnitude of the compressive force is a function of the stretch distance of the spring and a predetermined spring constant for the screw.

For a constant strain, the stress in a conventional bone screw normally drops off rapidly with time. However, the screw of the invention continuously corrects for stress relaxation, such that with the passage of time, the compression between the fragments is compensated by the screw and not by the behavior of the bone. While the tension in a conventional screw decreases exponentially, the tension in the bone screw of the invention decreases linearly with time and at a rate that is designed into the screw.

For purposes of the invention, any biocompatible material will suffice that has acceptable stress/strain characteristics, including titanium and composite materials.

In short, when fragments of a bone to be mended are displaced after tightening of the screw of the invention, energy is stored in the screw in an elastic, not rigid, manner such that fragments are forced to return in a gentle, but firm fashion to their original relative dispositions. Hence, the screw of the invention is a dynamic fixation device.

Applications for such a device include, but are not to be limited to, compression hip screws, cortical screws used with plates for long bone fractures, cancellous fixation of proximal tibia fractures, and repair of distal condylar femoral fractures as well as screws for securing total hip acetabular components and total shoulder glenoid components.

Other and further features, objects, advantages, and benefits of the invention will become apparent from the following description taken in conjunction with the following drawings. It is to be understood that the foregoing general description and the following detailed description are exemplary and explanatory but are not to be restrictive of the invention. The accompanying drawings which are incorporated in and constitute a part of the invention, illustrate some of the embodiments of the invention and, together with the description, serve to explain the principles of the invention in general terms. Like numerals refer to like parts throughout the disclosure.

BRIEF DESCRIPTION OF THE DRAWINGS

FIG. 1 is a detail cross section view illustrating the use of a conventional bone screw for adjoining a pair of bone fragments;

FIG. 2 is a graph depicting tension in a bone screw as a function of time to thereby indicate the stress relaxation which is experienced by different designs of bone screws;

FIG. 3 is a detail side elevation view of a conventional bone screw awaiting modification in accordance with the invention;

FIG. 4 is a side elevation view depicting an intermediate modification of the bone screw illustrated in FIG. 3;

DETAILED DESCRIPTION OF THE PREFERRED EMBODIMENT

Figure 5:
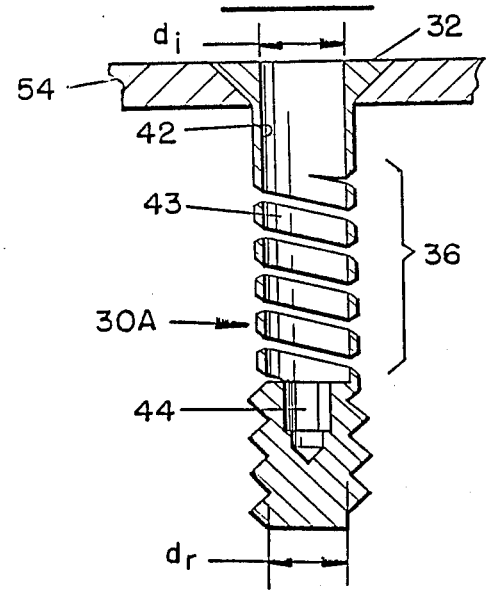
FIG. 5 is a side elevation view of a fully modified bone screw in accordance with the invention.

It was earlier explained that a primary goal of the invention is to provide a substantially constant force between bone fragments to enhance fracture fixation but that bone screws presently in use substantially fail in achieving this goal. Turn now to FIG. 1 for an explanation of the difficulties previously experienced. That figure generally illustrates a pair of bone fragments 20 and 22 which are intended to be joined by means of a conventional screw 24. In a customary fashion, a suitable torsion T is applied to the screw 24 to achieve a desired force F for holding the fragments 20, 22 together. The force F imparted to the bone fragments simultaneously imposes a similar reactive force, or tension, to the screw 24 and this produces a strain $\Delta l/l$ as indicated in FIG. 1. In this scenario, $$F = k\Delta l$$

where k is the spring constant and $\Delta l$ is a function of time, as dictated by the properties of the bone of which the fragments 20, 22 are composed.

Unfortunately, since the bone, as previously explained, "stress relaxes" immediately after the screw 24 has been tightened, there is an immediate and rapid reduction of the screw tension and, hence, of the force holding the fragments together. This situation is clearly illustrated in FIG. 2 which presents the relationship between the tension in the screw and the elapsed time following initial tightening of the screw to hold the fragments together. In the graph presented in FIG. 2, a curve 26 represents the ideal situation in which the tension in the screw, and therefore the force imparted to the bone fragments, remains constant for a long period of time. A curve 28, in contrast, illustrates the rapid, non-linear, rate of reduction of tension in the screw 24 which occurs as soon as the screw has been tightened.

It was for the purpose of providing a bone screw with the characteristics as close to that of curve 26 that the present invention was conceived and has now been reduced to practice Turn now to FIG. 3 which depicts a known bone screw 30 before being modified in accordance with the invention. The screw 30 has a head member 32 and a threaded shank 34 with an outer diameter $d_o$. According to the invention, an appropriate length 36 (see FIG. 4) of the shank 34 is milled to remove the outermost peak 38 of the threads formed on the shank. The result is an intermediate segment 36 having a diameter $d_m$ which is somewhat reduced from the outer diameter $d_o$ which remains for a distal end member 40 at an end of the screw opposite the head member 32.

After the modifications to the bone screw 30 have been accomplished as depicted in FIG. 4, it is further modified as depicted in FIG. 5. Specifically, an elongated bore 42 is formed, symmetrical with the longitudinal axis of the screw 30 and having a diameter slightly larger than the root diameter of the threads on the shank 34, that is, slightly larger than a diameter $d_r$. This perforation of the surface of the screw in a spiral fashion along the thread root results in the formation of a tension spring 43. The bore 42 extends as far as the distal end member 40 into which is suitably formed, symmetrical about a longitudinal axis of the screw 30, a tool receiving recess 44. The recess 44 may be sized and shaped to receive a hexagonal drive wrench of known design, although other shapes of recesses are deemed to be within the scope of the invention. Indeed, instead of a recess 44 being provided, some form of male member on the distal end member 40 may be contemplated to receive an appropriate tool for operating the bone screw in a manner which will be described. In any event, the modified bone screw depicted in FIG. 5, specifically, the bone screw of the invention, is indicated by the reference numeral 30A.

Figure 6:
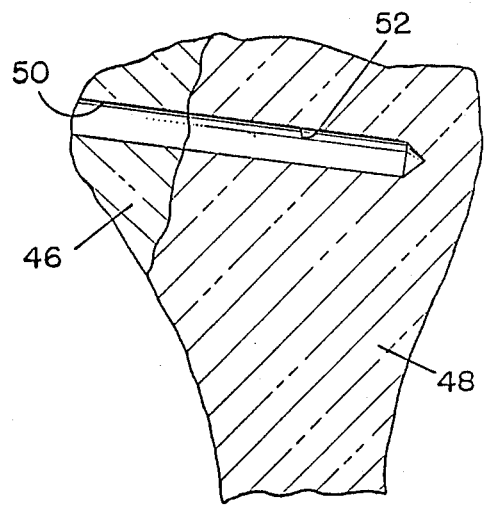
FIG. 6 is a detail cross section view of a pair of bone fragments prepared to receive the modified bone screw of the invention.
Figure 7:
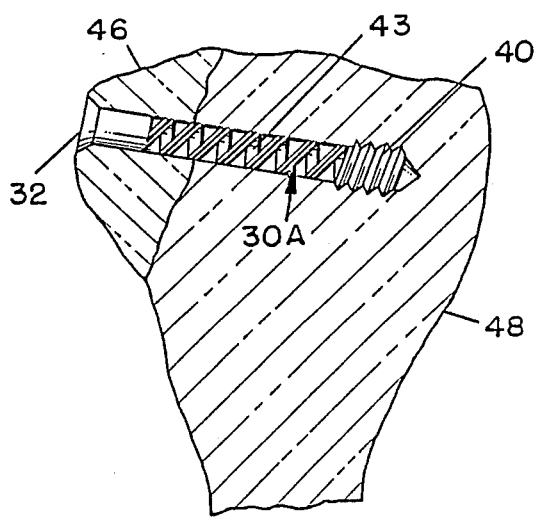
FIG. 7 is a detail cross section view, similar to FIG. 6, illustrating the use of the modified bone screw of the invention for joining the bone fragments together.

When it is desired to rejoin a pair of bone fragments 46, 48 as depicted in FIG. 6, suitable aligned bores 50, 52 are formed respectively in the fragments 46, 48. Thereupon, as seen in FIG. 7, with the modified bone screw 30A inserted into the bore 50, a suitable tool such as a hexagonal drive wrench (not shown) is inserted into the recess 44 to rotate the distal end member 40 around its longitudinal axis, and therefore, also the rest of the modified bone screw. With continued insertion of the modified bone screw 30A, the distal end member 40 eventually enters and advances along the bore 52 of the bone fragment 48. As the distal end member 40 continues to advance along the bore 52, the head member 32 moves into engagement with the outer surface of the bone fragment 46 such that continued advance of the distal end member 40 causes the spring 43 to stretch beyond its relaxed condition.

A suitable washer 54 may be interposed between the head member 32 and the bone fragment 46 (see FIG. 5), if desired, to reduce the unit loading being imposed on the exterior of the bone fragment. It will also be appreciated that while the foregoing description calls for the provision of the bores 50 and 52 to receive the modified bone screw 30A, the invention is sufficiently broad to encompass a situation in which the bores are not present and the bone screw 30A is of the self-tapping variety.

The force imposed on the bone fragments 46, 48 is a function of the spring rate and of the distance which the spring is stretched beyond its relaxed condition. The modified bone screw 30A, applied to the bone fragments 46, 48 in the manner depicted in FIG. 7, exhibits a stress relaxation having the nature illustrated by a curve 56 as presented in FIG. 2. That is, as the bone fragments 46, 48 undergo stress relaxation, the modified screw 30A similarly relaxes, while continuing to hold the fragments 46, 48 together.

To explain the operation of the modified bone screw 30A in greater detail it is noteworthy that for a given strain imparted by the modified bone screw, the force between the fragments (that is, the tension in the screw) decreases in a linear fashion because of the spring constant. As the bone relaxes by a length $\Delta l$, the spring will respond to a force equal to k $\Delta l$, such that the bone screw 30A will relax to that extent. The concept of the invention is that the modified bone screw 30A continues to accommodate the stress relaxation of the bone fragments until the fracture therebetween has completely healed.

Although the modified bone screw 30A has been described as being fabricated in a preferred manner, the invention is intended to encompass other fabrication techniques. For example, it can be envisioned that the spring 43 may be a separate component joined in some suitable manner, as by welding, to the head member 32 and to the distal end member 40.

While a preferred embodiment of the invention has been disclosed in detail, it should be understood by those skilled in the art that various other modifications may be made to the illustrated embodiment without departing from the scope of the invention as described in the specification and defined in the appended claims.

I claim:

1. A method of making a dynamic fixation screw comprising the steps of:
   providing an elongated screw having a longitudinal axis and an axially aligned head member and a threaded shank;
   reducing the outer diameter of a predetermined length of the threaded shank and thereby simultaneously forming a distal end member distant from the head member as well as a reduced-diameter intermediate shank portion between said head and distal end members; and boring said head member and said reduced-diameter intermediate shank portion along the longitudinal axis of said screw to a diameter that slightly exceeds the root diameter of the threads in said reduced-diameter intermediate shank portion thereby forming a tension spring integral with and intermediate the head member and the distal end member.

2. A method of making a dynamic fixation screw as set forth in claim 1 including the step of forming a tool receiving recess in the distal end member coaxial with the longitudinal axis.

* * * * *